(12) United States Patent
Dhar et al.

(10) Patent No.: US 12,139,734 B2
(45) Date of Patent: Nov. 12, 2024

(54) COMPOSITIONS AND METHODS FOR RNA SYNTHESIS

(71) Applicant: Helix Nanotechnologies Inc, Boston, MA (US)

(72) Inventors: Nikhil Dhar, Boston, MA (US); Nikolai Eroshenko, Boston, MA (US); Hannu Rajaniemi, Point Richmond, CA (US)

(73) Assignee: Helix Nanotechnologies Inc, Boston, MA (US)

( * ) Notice: Subject to any disclaimer, the term of this patent is extended or adjusted under 35 U.S.C. 154(b) by 253 days.

(21) Appl. No.: 17/246,451

(22) Filed: Apr. 30, 2021

(65) Prior Publication Data
US 2021/0363559 A1    Nov. 25, 2021

Related U.S. Application Data

(60) Provisional application No. 63/019,158, filed on May 1, 2020.

(51) Int. Cl.
*C12P 19/34*    (2006.01)
*C12N 9/12*    (2006.01)

(52) U.S. Cl.
CPC .......... *C12P 19/34* (2013.01); *C12N 9/1247* (2013.01); *C12Y 207/07006* (2013.01)

(58) Field of Classification Search
CPC ................. C12N 9/1247; C12P 19/34; C12Y 207/07006
See application file for complete search history.

(56) References Cited

U.S. PATENT DOCUMENTS

2008/0275219 A1    11/2008    Green et al.
2018/0009866 A1    1/2018    Hoge et al.

FOREIGN PATENT DOCUMENTS

WO    WO-2017109161 A1 *    6/2017    ............. C12N 15/10
WO    WO-2019/033095 A1    2/2019
WO    WO-2020/028729 A1    2/2020
WO    WO-2021/222856 A1    11/2021

OTHER PUBLICATIONS

Breckenridge et al. (Biotechnology and Bioengineering, 2000, 69(6):679-687) (Year: 2000).*
Wnendt et al. (Eur. J. Biochem., 1990, 191:467-472) (Year: 1990).*
International Search Report for PCT/US2021/030332, 3 pages (mailed Aug. 16, 2021).
Written Opinion for PCT/US2021/030332, 5 pages (mailed Aug. 16, 2021).
Gholamalipour, Y. et al., 3' end additions by T7 RNA polymerase are RNA self-templated, distributive and diverse in character-RNA-Seq analyses, NAR, 46(18):9253-9263 (2018).
Karikó, K. et al., Generating the optimal mRNA for therapy: HPLC purification eliminates immune activation and improves translation of nucleoside-modified, protein-encoding mRNA, NAR, 39(21):e142 (2011).
Karikó, K. et al., Incorporation of pseudouridine into mRNA yields superior nonimmunogenic vector with increased translational capacity and biological stability, Mol Ther., 16(11):1833-40 (2008).
Mu, X. et. al, An origin of the immunogenicity of in vitro transcribed, RNA, NAR, 46(10):5239-5249 (2018).
Wu, M. Z. et al., Synthesis of low immunogenicity RNA with high-temperature in vitro transcription, RNA, 26(3):345-360 (2020).

* cited by examiner

*Primary Examiner* — Jeremy C Flinders
(74) *Attorney, Agent, or Firm* — Choate, Hall & Stewart LLP; Stephanie L. Schonewald; Sowmya Subramanian

(57) ABSTRACT

Compositions and methods for synthesizing an RNA product are provided herein. For example, the present disclosure provides a method of producing an RNA product comprising incubating an in vitro transcription mixture, thereby producing an RNA product that comprises a plurality of single-stranded RNA molecules. In some embodiments, an in vitro transcription mixture comprises a DNA template comprising an RNA polymerase promoter sequence operatively linked to a target sequence; at least one RNA polymerase that recognizes the RNA polymerase promoter sequence; a plurality of ribonucleotides comprising at least two different types of ribonucleotides, each type comprising a different nucleoside; and a transcription buffer comprising an osmolyte.

19 Claims, 4 Drawing Sheets
Specification includes a Sequence Listing.

COMPOSITIONS AND METHODS FOR RNA SYNTHESIS

CROSS-REFERENCE TO RELATED APPLICATIONS

This application claims the benefit of U.S. Provisional Application No. 63/019,158, filed May 1, 2020, the contents of which are hereby incorporated herein in their entirety.

SEQUENCE LISTING

The instant application contains a Sequence Listing which has been submitted electronically in ASCII format and is hereby incorporated by reference in its entirety. Said ASCII copy, created on Dec. 4, 2020, is named 2012611-0024_SL.txt and is 10,335 bytes in size.

BACKGROUND

RNA therapies, including mRNA therapies, have gained prominence in clinical settings. Accordingly, there is a need for methods of developing and/or synthesizing safe and effective RNA therapies.

SUMMARY

The present disclosure provides compositions and methods for high yield in vitro transcription. Among other things, the present disclosure provides an insight that one or more osmolytes can be used as a means to facilitate in vitro transcription (e.g., in vitro RNA transcription) at an elevated temperature with an RNA polymerase (e.g., a wild-type bacteriophage RNA polymerases) that do not normally function at such an elevated temperature in the absence of an osmolyte. The present disclosure further provides that technologies described herein (e.g., performing RNA transcription with a wild-type RNA polymerase in the presence of one or more osmolytes (e.g., ones described herein) at an elevated temperature (e.g., a temperature at which a wild-type RNA polymerase do not normally function in the absence of such one or more osmolytes) can produce RNA with reduced immunogenicity and/or cellular toxicity. Such properties can increase, e.g., the therapeutic potency of RNA product.

In some embodiments, technologies described herein may be particularly useful for production of mRNA, as a greater purity of synthesized RNA products can enable higher efficiency translation of the encoded proteins. Accordingly, in some embodiments, technologies described herein can be used to produce an RNA product, which in some embodiments may be or comprise mRNA. Examples of RNA products include, e.g., inhibitory RNAs, antisense oligonucleotides, gene therapies and vaccines.

Among other things, the present disclosure provides a method of producing an RNA product. In some embodiments, a method comprises a step of incubating an in vitro transcription mixture, thereby producing an RNA product that comprises a plurality of single-stranded RNA molecules. In some embodiments, an in vitro transcription mixture comprises a DNA template comprising an RNA polymerase promoter sequence operatively linked to a target sequence, at least one RNA polymerase that recognizes the RNA polymerase promoter sequence, a plurality of ribonucleotides comprising at least two different types of ribonucleotides, each type comprising a different nucleoside, and a transcription buffer comprising an osmolyte.

In some embodiments, an osmolyte is or comprises an amino acid-based osmolyte, a methylamine osmolyte, a carbohydrate osmolyte, or a combination thereof.

In some embodiments, a methylamine osmolyte, is or comprises glycerophosphorylcholine trimethylamine N-oxide, or a combination thereof.

In some embodiments, a carbohydrate osmolyte is or comprises sorbitol, glycerol, myonisitol, diglycerol phosphate, or a combination thereof.

In some embodiments, an amino acid-based osmolyte is or comprises a proline-based osmolyte, a glycine-based osmolyte, an ectoine-based osmolyte, an alanine-based osmolyte, or a combination thereof.

In some embodiments, an alanine-based osmolyte is or comprises beta-alanine. In some embodiments, an amino acid-based osmolyte is or comprises a glycine-based osmolyte. In some embodiments, a glycine-based osmolyte is or comprises betaine.

In some embodiments, betaine is present in the in vitro transcription mixture at a concentration of at least 0.25M, at least 0.5M, at least 0.75M, at least 1M, at least 1.5M, at least 2M or at least 2.5M. In some embodiments, betaine is present in the in vitro transcription mixture at a concentration of at most 15M, at most 10M, at least 5M, or at least 2.5M. In some embodiments, betaine is present in the in vitro transcription mixture at a concentration of about 0.5M to about 10M, or about 2M to about 5M.

In some embodiments, an RNA polymerase is or comprises a bacteriophage RNA polymerase. In some embodiments, a bacteriophage RNA polymerase is a T7 RNA polymerase, a T3 RNA polymerase, a SP6 RNA polymerase, a N4 virion RNA polymerase, or a variant thereof. In some embodiments, a bacteriophage RNA polymerase is or comprises a T7 RNA polymerase.

In some embodiments, an incubating step occurs at a temperature of at least 37° C.

In some embodiments, a T7 RNA polymerase is a wild-type T7 RNA polymerase and an incubating step occurs at a temperature of about 45° C., 46° C., 47° C., 48° C., 49° C., 50° C., 51° C., 52° C., 53° C., 54° C., 55° C., or higher.

In some embodiments, a plurality of single-stranded RNA molecules are or comprise guide RNA, short hairpin RNA, siRNA, microRNA, long non-coding RNA, or messenger RNA (mRNA). In some embodiments, a plurality of single-stranded RNA molecules are or comprise mRNA molecules encoding one or more target polypeptides.

In some embodiments, mRNA molecules include a 5' cap.

In some embodiments, a plurality of single-stranded RNA molecules comprise one or more ribonucleotides that each include a modified nucleoside.

In some embodiments, an RNA product is less immunostimulatory than an RNA product produced in the absence of the osmolyte at an incubation temperature of about 37° C.

In some embodiments, an RNA product has a lower level of double-stranded RNA than that in an RNA product produced in the absence of the osmolyte at an incubation temperature of about 37° C.

In some embodiments, a method described herein does not comprise a step of removing any double-stranded RNA from the RNA product.

In some embodiments, an RNA product has a higher amount of single-stranded RNA molecules than that in an RNA product produced in the absence of the osmolyte at an incubation temperature of about 37° C. In some embodiments, an amount of single-stranded RNA molecules is a percentage of single-stranded RNA molecules in an RNA product.

In some embodiments, a method described herein comprises removing DNA from the in vitro transcription mixture after the incubating step. In some embodiments, removing comprises adding a DNase to the in vitro transcription mixture after the incubating step.

In some embodiments, a DNA template is immobilized on a solid substrate. In some embodiments, removing DNA comprises separating the solid substrate from the in vitro transcription mixture. In some embodiments, a solid substrate is a bead.

In some embodiments, a plurality of single-stranded RNA molecules each have a length of at least 100 nucleotides or longer, e.g., at least 200 nucleotides, at least 300 nucleotides, at least 400 nucleotides, at least 500 nucleotides, or longer. In some embodiments, a plurality of single-stranded RNA molecules each have a length of no more than 200,000 nucleotides, nor more than 150,000 nucleotides, no more than 100,000 nucleotides, or no more than 50,000 nucleotides.

In some embodiments, an incubating step is performed for a time sufficient for a target sequence to be transcribed to a single-stranded RNA molecule.

In some embodiments, an incubating step is performed for at least 1 hour, at least 2 hours, at least 3 hours, at least 4 hours, or longer.

The present disclosure provides a method comprising contacting one or more host cells (e.g., mammalian cells) with a composition comprising an RNA product produced by a method as described herein.

In some embodiments, an RNA product in the composition is less immunostimulatory than an RNA product produced in the absence of the osmolyte at an incubation temperature of about 37° C.

In some embodiments, one or more host cells (e.g., mammalian cells) are present in a cell culture. In some embodiments, a cell culture is an in vitro cell culture. In some embodiments, a cell culture is an ex vivo cell culture.

In some embodiments, one or more host cells (e.g., mammalian cells) are present in a subject. In some embodiments, a contacting step comprises administering to the subject the composition.

In some embodiments, composition is a pharmaceutical composition. In some embodiments, a pharmaceutical composition further comprises a pharmaceutically acceptable excipient.

In some embodiments, a method as described herein increases a level of expression from the single-stranded RNA molecule(s), as compared to a level of expression from single-stranded RNA molecule(s) in an RNA product produced in the absence of the osmolyte at an incubation temperature of about 37° C.

In some embodiments, a method as described herein increases the viability of the one or more host cells (e.g., mammalian cells) following contact with the RNA product, as compared to the viability of one or more host cells (e.g., mammalian cells) contacted with an RNA product produced in the absence of the osmolyte at an incubation temperature of about 37° C.

The present disclosure also provides an in vitro transcription mixture. In some embodiments, an in vitro transcription mixture comprises a DNA template comprising an RNA polymerase promoter sequence operatively linked to a target sequence. In some embodiments, an in vitro transcription mixture comprises a wild-type bacteriophage RNA polymerase that recognizes the RNA polymerase promoter sequence. In some embodiments, an in vitro transcription mixture comprises a plurality of ribonucleotides comprising at least two different types of ribonucleotides, each type comprising a different nucleoside. In some embodiments, an in vitro transcription mixture comprises a transcription buffer comprising an osmolyte comprising an amino acid-based osmolyte, a methylamine osmolyte, a carbohydrate osmolyte, or a combination thereof.

In some embodiments, a methylamine osmolyte is or comprises glycerophosphorylcholine, trimethylamine N-oxide, or a combination thereof.

In some embodiments, a carbohydrate osmolyte is or comprises sorbitol, glycerol, myonisitol, diglycerol phosphate, or a combination thereof.

In some embodiments, an amino acid-based osmolyte is or comprises a proline-based osmolyte, a glycine-based osmolyte, an ectoine-based osmolyte, an alanine-based osmolyte, or a combination thereof. In some embodiments, an alanine-based osmolyte is or comprises beta-alanine. In some embodiments, an amino acid-based osmolyte is or comprises a glycine-based osmolyte. In some embodiments, a glycine-based osmolyte is or comprises betaine.

In some embodiments, a wild-type bacteriophage RNA polymerase is or comprises a wild-type T7 RNA polymerase.

The present disclosure provides a composition comprising an RNA product. In some embodiments, an RNA product is produced by a method as described herein.

In some embodiments, an RNA product comprises guide RNA, short hairpin RNA, siRNA, microRNA, long non-coding RNA, or messenger RNA (mRNA). In some embodiments, an RNA product comprises mRNA molecules encoding one or more target polypeptides. In some embodiments, mRNA molecules include a 5' cap.

In some embodiments, an RNA product comprises a plurality of single-stranded RNA molecules that comprise one or more ribonucleotides that each include a modified nucleoside.

In some embodiments, an RNA product is less immunostimulatory than an RNA product produced in the absence of the osmolyte at an incubation temperature of about 37° C.

In some embodiments, an RNA product has a lower level of double-stranded RNA than that in an RNA product produced in the absence of the osmolyte at an incubation temperature of about 37° C.

In some embodiments, an RNA product has a higher amount of single-stranded RNA molecules than that in an RNA product produced in the absence of the osmolyte at an incubation temperature of about 37° C. In some embodiments, an amount of single-stranded RNA molecules is a percentage of single-stranded RNA molecules in an RNA product.

In some embodiments, composition is a pharmaceutical composition. In some embodiments, a pharmaceutical composition further comprises a pharmaceutically acceptable excipient.

CERTAIN DEFINITIONS

Figure 1:
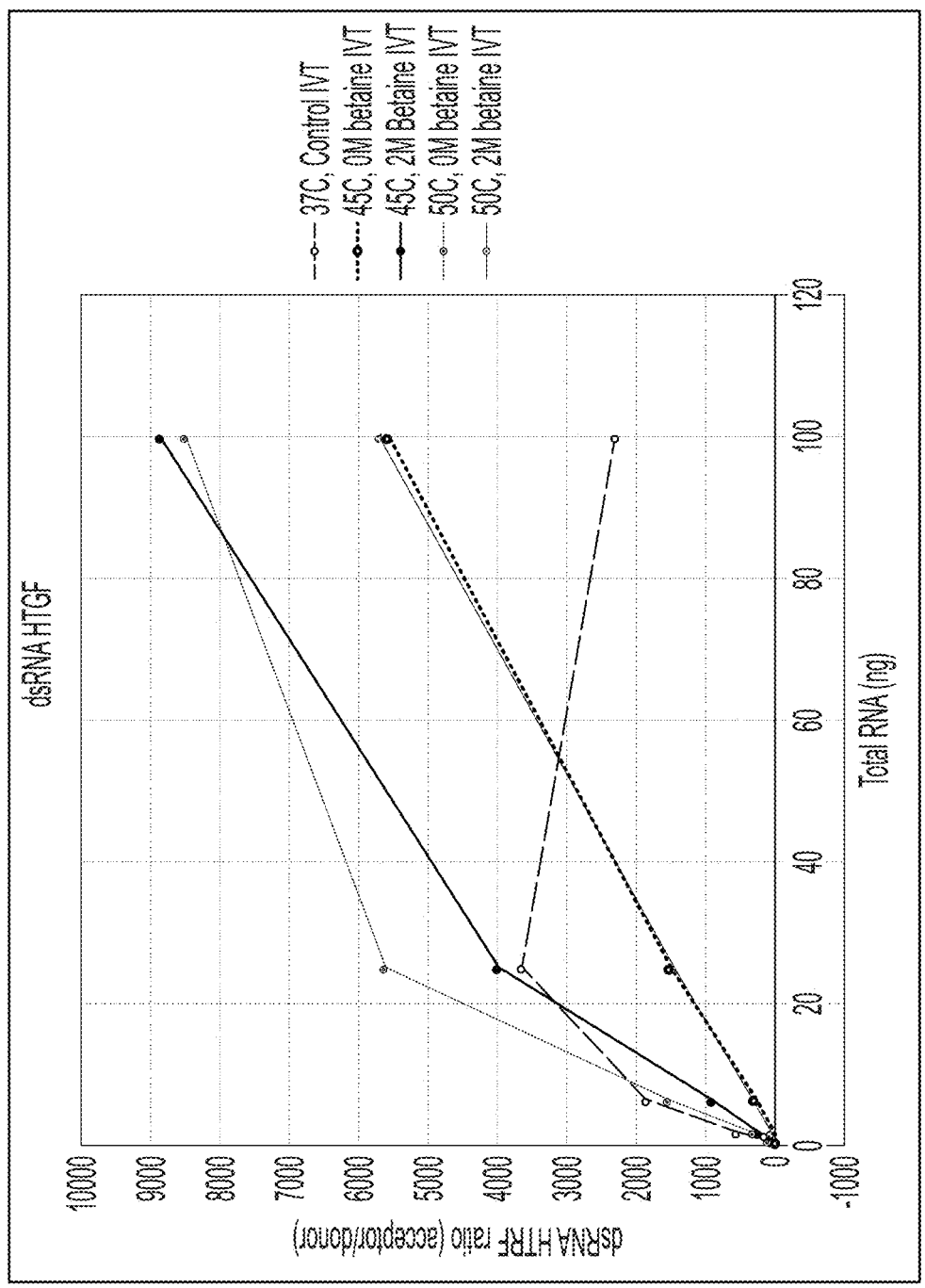
FIG. 1 includes a line graph showing a yield of double-stranded DNA from an exemplary T7 synthesis preparation as described herein with and without betaine at 37° C., 45° C. and 50° C.

In this application, unless otherwise clear from context, (i) the term "a" may be understood to mean "at least one"; (ii) the term "or" may be understood to mean "and/or"; (iii) the terms "comprising" and "including" may be understood to encompass itemized components or steps whether presented by themselves or together with one or more additional components or steps; and (iv) where ranges are provided, endpoints are included.

About or approximately: As used herein, the terms "about" and "approximately," when used herein in reference to a value, refers to a value that is similar, in context to the referenced value. In general, those skilled in the art, familiar with the context, will appreciate the relevant degree of variance encompassed by "about" or "approximately" in that context. For example, in some embodiments, the term "about" or "approximately" may encompass a range of values that within 25%, 20%, 19%, 18%, 17%, 16%, 15%, 14%, 13%, 12%, 11%, 10%, 9%, 8%, 7%, 6%, 5%, 4%, 3%, 2%, 1%, or less of the referred value.

Administration: As used herein, the term "administration" typically refers to the administration of a composition to a cell, tissue, subject or system, for example to achieve delivery of a product that is, or is included in or otherwise delivered by, the composition. Those of ordinary skill in the art will be aware of a variety of routes that may, in appropriate circumstances, be utilized for administration to a subject, for example a mammal, e.g., a human. For example, in some embodiments, administration may be ocular, oral, parenteral, topical, etc. In some particular embodiments, administration may be bronchial (e.g., by bronchial instillation), buccal, dermal (which may be or comprise, for example, one or more of topical to the dermis, intradermal, interdermal, transdermal, etc), enteral, intra-arterial, intradermal, intragastric, intramedullary, intramuscular, intranasal, intraperitoneal, intrathecal, intravenous, intraventricular, within a specific organ (e. g. intrahepatic), mucosal, nasal, oral, rectal, subcutaneous, sublingual, topical, tracheal (e.g., by intratracheal instillation), vaginal, vitreal, etc. In some embodiments, administration may involve only a single dose. In some embodiments, administration may involve application of a fixed number of doses. In some embodiments, administration may involve dosing that is intermittent (e.g., a plurality of doses separated in time) and/or periodic (e.g., individual doses separated by a common period of time) dosing. In some embodiments, administration may involve continuous dosing (e.g., perfusion) for at least a selected period of time.

Comparable: As used herein, the term "comparable" refers to two or more agents, entities, situations, sets of conditions, etc., that may not be identical to one another but that are sufficiently similar to permit comparison therebetween so that one skilled in the art will appreciate that conclusions may reasonably be drawn based on differences or similarities observed. In some embodiments, comparable sets of conditions, circumstances, individuals, or populations are characterized by a plurality of substantially identical features and one or a small number of varied features. Those of ordinary skill in the art will understand, in context, what degree of identity is required in any given circumstance for two or more such agents, entities, situations, sets of conditions, etc. to be considered comparable. For example, those of ordinary skill in the art will appreciate that sets of circumstances, individuals, or populations are comparable to one another when characterized by a sufficient number and type of substantially identical features to warrant a reasonable conclusion that differences in results obtained or phenomena observed under or with different sets of circumstances, individuals, or populations are caused by or indicative of the variation in those features that are varied.

Expression: As used herein, the term "expression" of a nucleic acid sequence refers to the generation of any gene product from the nucleic acid sequence. In some embodiments, a gene product can be a transcript. In some embodiments, a gene product can be a polypeptide. In some embodiments, expression of a nucleic acid sequence involves one or more of the following: (1) production of an RNA template from a DNA sequence (e.g., by transcription); (2) processing of an RNA transcript (e.g., by splicing, editing, etc); (3) translation of an RNA into a polypeptide or protein; and/or (4) post-translational modification of a polypeptide or protein.

Host cell: as used herein, refers to a cell into which exogenous DNA (recombinant or otherwise) has been introduced. Persons of skill upon reading this disclosure will understand that such terms refer not only to the particular subject cell, but also to the progeny of such a cell. Because certain modifications may occur in succeeding generations due to either mutation or environmental influences, such progeny may not, in fact, be identical to the parent cell, but are still included within the scope of the term "host cell" as used herein. In some embodiments, host cells include prokaryotic and eukaryotic cells selected from any of the Kingdoms of life that are suitable for expressing an exogenous DNA (e.g., a recombinant nucleic acid sequence). Exemplary cells include those of prokaryotes and eukaryotes (single-cell or multiple-cell), bacterial cells (e.g., strains of *E. coli, Bacillus* spp., *Streptomyces* spp., etc.), mycobacteria cells, fungal cells, yeast cells (e.g., *S. cerevisiae, S. pombe, P. pastoris, P. methanolica*, etc.), plant cells, insect cells (e.g., SF-9, SF-21, baculovirus-infected insect cells, *Trichoplusia ni*, etc.), non-human animal cells, human cells, or cell fusions such as, for example, hybridomas or quadromas. In some embodiments, the cell is a human, monkey, ape, hamster, rat, or mouse cell. In some embodiments, the cell is eukaryotic and is selected from the following cells: CHO (e.g., CHO Kl, DXB-11 CHO, Veggie-CHO), COS (e.g., COS-7), retinal cell, Vero, CV1, kidney (e.g., HEK293, 293 EBNA, MSR 293, MDCK, HaK, BHK), HeLa, HepG2, WI38, MRC 5, Colo205, HB 8065, HL-60, (e.g., BHK21), Jurkat, Daudi, A431 (epidermal), CV-1, U937, 3T3, L cell, C127 cell, SP2/0, NS-0, NT 060562, Sertoli cell, BRL 3 A cell, HT1080 cell, myeloma cell, tumor cell, and a cell line derived from an aforementioned cell. In some embodiments, the cell comprises one or more viral genes.

"Improve," "increase", "inhibit" or "reduce": As used herein, the terms "improve", "increase", "inhibit", "reduce", or grammatical equivalents thereof, indicate values that are relative to a baseline or other reference measurement. In some embodiments, an appropriate reference measurement may be or comprise a measurement in a particular system (e.g., in a single individual) under otherwise comparable conditions absent presence of (e.g., prior to and/or after) a particular agent or treatment, or in presence of an appropriate comparable reference agent. In some embodiments, an appropriate reference measurement may be or comprise a measurement in comparable system known or expected to respond in a particular way, in presence of the relevant agent or treatment.

Nucleic acid/Oligonucleotide: As used herein, the terms "nucleic acid" and "oligonucleotide" are used interchangeably, and refer to a polymer of at least 3 nucleotides or more. In some embodiments, a nucleic acid comprises DNA. In some embodiments, a nucleic acid comprises RNA. In some embodiments, a nucleic acid is single stranded. In some embodiments, a nucleic acid is double stranded. In some embodiments, a nucleic acid comprises both single and double stranded portions. In some embodiments, a nucleic acid comprises a backbone that comprises one or more phosphodiester linkages. In some embodiments, a nucleic acid comprises a backbone that comprises both phosphodiester and non-phosphodiester linkages. For example, in some embodiments, a nucleic acid may comprise a backbone that comprises one or more phosphorothioate or 5'-N-phosphoramidite linkages and/or one or more peptide bonds, e.g., as in a "peptide nucleic acid". In some embodiments, a nucleic acid comprises one or more, or all, natural residues (e.g., adenine, cytosine, deoxyadenosine, deoxycytidine, deoxyguanosine, deoxythymidine, guanine, thymine, uracil). In some embodiments, a nucleic acid comprises on or more, or all, non-natural residues. In some embodiments, a non-natural residue comprises a nucleoside analog (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, 6-O-methylguanine, 2-thiocytidine, methylated bases, intercalated bases, and combinations thereof). In some embodiments, a non-natural residue comprises one or more modified sugars (e.g., 2'-fluororibose, ribose, 2'-deoxyribose, arabinose, and hexose) as compared to those in natural residues. In some embodiments, a nucleic acid has a nucleotide sequence that encodes a functional gene product such as an RNA or polypeptide. In some embodiments, a nucleic acid has a nucleotide sequence that comprises one or more introns. In some embodiments, a nucleic acid may be prepared by isolation from a natural source, enzymatic synthesis (e.g., by polymerization based on a complementary template, e.g., in vivo or in vitro, reproduction in a recombinant cell or system, or chemical synthesis. In some embodiments, a nucleic acid is at least 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 20, 225, 250, 275, 300, 325, 350, 375, 400, 425, 450, 475, 500, 600, 700, 800, 900, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, or 20,000 or more residues or nucleotides long.

Nucleotide: As used herein, the term "nucleotide" refers to its art-recognized meaning. When a number of nucleotides is used as an indication of size, e.g., of an RNA oligonucleotide, a certain number of nucleotides refers to the number of nucleotides on a single strand, e.g., of an RNA oligonucleotide.

Pharmaceutical composition: As used herein, the term "pharmaceutical composition" refers to an active agent, formulated together with one or more pharmaceutically acceptable carriers. In some embodiments, active agent is present in unit dose amount appropriate for administration in a therapeutic regimen that shows a statistically significant probability of achieving a predetermined therapeutic effect when administered to a relevant population. In some embodiments, pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

Pharmaceutically acceptable: As used herein, the term "pharmaceutically acceptable" applied to the carrier, diluent, or excipient used to formulate a composition as disclosed herein means that the carrier, diluent, or excipient must be compatible with the other ingredients of the composition and not deleterious to the recipient thereof.

Polypeptide: The term "polypeptide", as used herein, generally has its art-recognized meaning of a polymer of at least three amino acids or more. Those of ordinary skill in the art will appreciate that the term "polypeptide" is intended to be sufficiently general as to encompass not only polypeptides having a complete sequence recited herein, but also to encompass polypeptides that represent functional, biologically active, or characteristic fragments, portions or domains (e.g., fragments, portions, or domains retaining at least one activity) of such complete polypeptides. Polypeptides may contain L-amino acids, D-amino acids, or both and may contain any of a variety of amino acid modifications or analogs known in the art. Useful modifications include, e.g., terminal acetylation, amidation, methylation, etc. In some embodiments, polypeptides may comprise natural amino acids, non-natural amino acids, synthetic amino acids, and combinations thereof.

RNA oligonucleotide: As used herein, the term "RNA oligonucleotide" refers to an oligonucleotide of ribonucleotides. In some embodiments, an RNA oligonucleotide is single stranded. In some embodiments, an RNA oligonucleotide is double stranded. In some embodiments, an RNA oligonucleotide comprises both single and double stranded portions. In some embodiments, an RNA oligonucleotide can comprise a backbone structure as described in the definition of "Nucleic acid Oligonucleotide" above. An RNA oligonucleotide can be a regulatory RNA (e.g., siRNA, microRNA, etc.), or a messenger RNA (mRNA) oligonucleotide. In some embodiments where an RNA oligonucleotide is a mRNA oligonucleotide, an RNA oligonucleotide typically comprises at its 3' end a poly(A) region. In some embodiments where an RNA oligonucleotide is a mRNA oligonucleotide, an RNA oligonucleotide typically comprises at its 5' end an art-recognized cap structure, e.g., for recognizing and attachment of a mRNA to a ribosome to initiate translation.

Standard techniques may be used for recombinant DNA, oligonucleotide synthesis, e.g., mRNA synthesis, and tissue culture and transformation (e.g., electroporation, lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al., Molecular Cloning: A Laboratory Manual (2nd ed., Cold Spring Harbor Laboratory Press, Cold Spring Harbor, N.Y. (1989)), which is incorporated herein by reference for any purpose.

Subject: As used herein, the term "subject" refers an organism, typically a mammal (e.g., a human, in some embodiments including prenatal human forms). In some embodiments, a subject is suffering from a relevant disease, disorder or condition. In some embodiments, a subject is susceptible to a disease, disorder, or condition. In some embodiments, a subject displays one or more symptoms or characteristics of a disease, disorder or condition. In some embodiments, a subject does not display any symptom or characteristic of a disease, disorder, or condition. In some embodiments, a subject is someone with one or more features characteristic of susceptibility to or risk of a disease, disorder, or condition. In some embodiments, a subject is a patient. In some embodiments, a subject is an individual to whom diagnosis and/or therapy is and/or has been administered.

DETAILED DESCRIPTION OF CERTAIN EMBODIMENTS

A significant challenge for the clinical viability of mRNA therapies is reducing the innate immune response to exogenous RNA. A large part of the innate immune response to these therapies is driven by recognition of various contaminants produced during in vitro transcription. RIG-I is responsible for detection of uncapped ssRNA and dsRNA, while MDA5 and PKR can detect small aberrant transcripts and large dsRNA side products. Bypassing recognition by these sensors is crucial for RNA based therapies since innate immune signaling converges on pathways of NF-kB and IRF upregulation. PKR signaling on its own directly reduces global protein synthesis by inhibition of the translational machinery. Activation of these pathways ultimately leads to the establishment of an anti-viral state that can lead to decreased efficacy of mRNA delivered therapy.

Substantial work has been conducted to address this issue including the use of chemically modified nucleotides (Karikó et al., Mol Ther. 2008, which is incorporated herein by reference in its entirety) that reduce the ability of innate immune sensors to detect synthetic RNA and HPLC purification to directly remove contaminants from the preparation (Karikó, Muramatsu, Ludwig, & Weissman, NAR 2011, which is incorporated herein by reference in its entirety). Unfortunately, HPLC purification can be expensive and result in less than optimal yield due to loss of sample during the process, which become non-trivial issues at large scales of synthesis. The use of chemically modified nucleotides is complicated by the need for licensing agreements for their use in commercial applications. More recent work on optimization of in vitro transcription conditions has provided RNA with reduced immunogenicity (Mu, et. al, NAR 2018, which is incorporated herein by reference in its entirety), but with the downside of lower yields that can also become prohibitive for large scale synthesis.

In some embodiments, the present disclosure provides technologies that address the issue of reducing innate immune response to our mRNA therapies while maintaining high yields from in vitro transcription that allow for large scale synthesis. An initial hypothesis was that in vitro transcription at elevated temperatures may reduce the synthesis of dsRNA side products by any number of mechanisms. Some conceivable mechanisms include reduced non-specific binding of RNA polymerase to the DNA template and decreased re-initiation of the polymerase at the non-promoter end of the template. These mechanisms are consistent with the discovery that IVT sense RNA can rebind the polymerase and self-prime in cis (Gholamalipour, Mudiyanselage, & Martin NAR 2018, which is incorporated herein by reference in its entirety) and that the resulting hairpin that is generated can compete with promoter dependent T7 initiation under high yield IVT conditions. Wu, Asahara, Tzertzinis, & Roy, R N A 2020 (which is incorporated herein by reference in its entirety) recently reported that high temperature in vitro transcription with thermostable T7 RNA polymerase variants can reduce the synthesis of dsRNA byproducts by reducing self-priming of the in vitro transcription product. That work relied on the design of novel thermostable T7 promoter-dependent RNA polymerases since wild-type T7 RNA polymerase is inactive at temperatures above 45 C. While glycine-based osmolytes have been shown to help stabilize proteins at high temperature (Santoro, et al. Biochemistry 1992, which is incorporated herein by reference in its entirety), there remains a need in the field for high yield methods to synthesize stable RNA.

The present disclosure provides compositions and methods for high yield in vitro transcription. In particular, the present disclosure provides the insight that the addition of an osmolyte, e.g., betaine, to in vitro transcription reactions allows for high yield synthesis of RNAs, e.g., while using wild-type T7 RNA polymerase at temperatures at an elevated temperature, e.g., above 45 C. Further, the present disclosure provides that RNAs produced by in vitro transcription in the presence of an osmolyte can have reduced immunogenicity and/or high expression.

Exemplary Methods for Producing an RNA Product

Among other things, the present disclosure provides a method of producing an RNA product. In some embodiments, a method comprises a step of incubating an in vitro transcription mixture, thereby producing an RNA product that comprises a plurality of single-stranded RNA molecules. In some embodiments, an in vitro transcription mixture comprises a DNA template comprising an RNA polymerase promoter sequence operatively linked to a target sequence, at least one RNA polymerase that recognizes the RNA polymerase promoter sequence, a plurality of ribonucleotides comprising at least two different types of ribonucleotides, each type comprising a different nucleoside, and a transcription buffer comprising an osmolyte.

In some embodiments, an osmolyte is or comprises an amino acid-based osmolyte, a methylamine osmolyte, a carbohydrate osmolyte, or a combination thereof. In some embodiments, a methylamine osmolyte, is or comprises glycerophosphorylcholine trimethylamine N-oxide, or a combination thereof. In some embodiments, a carbohydrate osmolyte is or comprises sorbitol, glycerol, myonisitol, diglycerol phosphate, or a combination thereof. In some embodiments, an amino acid-based osmolyte is or comprises a proline-based osmolyte, a glycine-based osmolyte, an ectoine-based osmolyte, an alanine-based osmolyte, or a combination thereof. In some embodiments, an alanine-based osmolyte is or comprises beta-alanine. In some embodiments, an amino acid-based osmolyte is or comprises a glycine-based osmolyte. In some embodiments, a glycine-based osmolyte is or comprises betaine.

In some embodiments, betaine is present in the in vitro transcription mixture at a concentration of at least 0.25M, at least 0.5M, at least 0.75M, at least 1M, at least 1.5M, at least 2M or at least 2.5M. In some embodiments, betaine is present in the in vitro transcription mixture at a concentration of at most 15M, at most 10M, at least 5M, or at least 2.5M. In some embodiments, betaine is present in the in vitro transcription mixture at a concentration of about 0.5M to about 10M, or about 2M to about 5M.

In some embodiments, an RNA polymerase is or comprises a bacteriophage RNA polymerase. In some embodiments, a bacteriophage RNA polymerase is a T7 RNA polymerase, a T3 RNA polymerase, a SP6 RNA polymerase, a N4 virion RNA polymerase, or a variant thereof. In some embodiments, a bacteriophage RNA polymerase is or comprises a T7 RNA polymerase.

In some embodiments, an incubating step occurs at a temperature of at least 37° C., at least 40° C., at least 45° C., at least 46° C., at least 47° C., at least 48° C., at least 49° C., at least 50° C., at least 51° C., at least 52° C., at least 53° C., at least 54° C., at least 55° C., at least 60° C., or at least 65° C. In some embodiments, an incubating step occurs at a temperature of at most 75° C., at most 70° C., at most 65° C., at most 60° C., at most 59° C., at most 58° C., at most 57° C., at most 56° C., or at most 55° C.

In some embodiments, a T7 RNA polymerase is a wild-type T7 RNA polymerase and an incubating step occurs at a temperature of about 45° C., 46° C., 47° C., 48° C., 49° C., 50° C., 51° C., 52° C., 53° C., 54° C., 55° C., or higher.

In some embodiments, a plurality of single-stranded RNA molecules are or comprise guide RNA, short hairpin RNA, siRNA, microRNA, long non-coding RNA, or messenger RNA (mRNA). In some embodiments, a plurality of single-stranded RNA molecules are or comprise mRNA molecules encoding one or more target polypeptides. In some embodiments, mRNA molecules include a 5' cap. In some embodiments, mRNA molecules include a poly-A tail. In some embodiments, mRNA molecules comprise at least one intron. In some embodiments, mRNA molecules comprise at least one untranslated region.

In some embodiments, a plurality of single-stranded RNA molecules comprise one or more ribonucleotides that each include a modified nucleoside.

In some embodiments, an RNA product is less immuno-stimulatory than an RNA product produced in the absence of the osmolyte. In some embodiments, an RNA product produced in the absence of the osmolyte is produced at an incubation temperature of about 37° C.

In some embodiments, an RNA product has a lower level of double-stranded RNA than that in an RNA product produced in the absence of the osmolyte. In some embodiments, an RNA product produced in the absence of the osmolyte is produced at an incubation temperature of about 37° C.

In some embodiments, a method described herein does not comprise a step of removing any double-stranded RNA from the RNA product.

In some embodiments, an RNA product has a higher amount of single-stranded RNA molecules than that in an RNA product produced in the absence of the osmolyte. In some embodiments, an RNA product produced in the absence of the osmolyte is produced at an incubation temperature of about 37° C. In some embodiments, an amount of single-stranded RNA molecules is a percentage of single-stranded RNA molecules in an RNA product. In some embodiments, an amount of single-stranded RNA molecules is a number of single-stranded RNA molecules in an RNA product.

In some embodiments, a method described herein comprises removing DNA from the in vitro transcription mixture, e.g., after the incubating step. In some embodiments, removing comprises adding a DNase to the in vitro transcription mixture after the incubating step.

In some embodiments, a DNA template is immobilized on a solid substrate. In some embodiments, removing DNA comprises separating the solid substrate from the in vitro transcription mixture. In some embodiments, a solid substrate is a bead.

In some embodiments, a plurality of single-stranded RNA molecules each have a length of at least 100 nucleotides or longer, e.g., at least 200 nucleotides, at least 300 nucleotides, at least 400 nucleotides, at least 500 nucleotides, or longer. In some embodiments, a plurality of single-stranded RNA molecules each have a length of no more than 200,000 nucleotides, nor more than 150,000 nucleotides, no more than 100,000 nucleotides, or no more than 50,000 nucleotides.

In some embodiments, an incubating step is performed for a time sufficient for a target sequence to be transcribed to a single-stranded RNA molecule. In some embodiments, an incubating step is performed for at least 1 hour, at least 2 hours, at least 3 hours, at least 4 hours, or longer.

Exemplary Compositions Comprising an RNA Product

The present disclosure provides compositions comprising an RNA product. In some embodiments, an RNA product is produced by a method as described herein.

In some embodiments, an RNA product comprises guide RNA, short hairpin RNA, siRNA, microRNA, long non-coding RNA, or messenger RNA (mRNA). In some embodiments, an RNA product comprises mRNA molecules encoding one or more target polypeptides. In some embodiments, mRNA molecules include a 5' cap.

In some embodiments, an RNA product comprises a plurality of single-stranded RNA. In some embodiments, a plurality of single-stranded RNA molecules can comprise one or more ribonucleotides that each include a modified nucleoside.

In some embodiments, a plurality of single-stranded RNA molecules each have a length of at least 100 nucleotides or longer, e.g., at least 200 nucleotides, at least 300 nucleotides, at least 400 nucleotides, at least 500 nucleotides, or longer. In some embodiments, a plurality of single-stranded RNA molecules each have a length of no more than 200,000 nucleotides, nor more than 150,000 nucleotides, no more than 100,000 nucleotides, or no more than 50,000 nucleotides.

In some embodiments, an RNA product is less immuno-stimulatory than an RNA product produced in the absence of an osmolyte, e.g., an RNA product produced in the absence of an osmolyte and at an incubation temperature of about 37° C.

In some embodiments, an RNA product has a lower level of double-stranded RNA than that in an RNA product produced in the absence of the osmolyte, e.g., an RNA product produced in the absence of an osmolyte and at an incubation temperature of about 37° C.

In some embodiments, an RNA product has a higher amount of single-stranded RNA molecules than that in an RNA product produced in the absence of the osmolyte, e.g., an RNA product produced in the absence of an osmolyte and at an incubation temperature of about 37° C. In some embodiments, an amount of single-stranded RNA molecules is a percentage of single-stranded RNA molecules in an RNA product.

In some embodiments, composition is a pharmaceutical composition. In some embodiments, a pharmaceutical composition further comprises a pharmaceutically acceptable excipient.

In some embodiments, a pharmaceutical composition can include a pharmaceutically acceptable carrier or excipient, which, as used herein, includes any and all solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Remington's The Science and Practice of Pharmacy, 21st Edition, A. R. Gennaro (Lippincott, Williams & Wilkins, Baltimore, MD, 2006; incorporated herein by reference) discloses various excipients used in formulating pharmaceutical compositions and known techniques for the preparation thereof. Suitable pharmaceutically acceptable carriers include but are not limited to water, salt solutions (e.g., NaCl), saline, buffered saline, glycerol, sugars such as mannitol, sucrose, or others, dextrose, fatty acid esters, etc., as well as combinations thereof.

A pharmaceutical composition can, if desired, be mixed with auxiliary agents (e.g., lubricants, preservatives, stabilizers, wetting agents, emulsifiers, salts for influencing osmotic pressure, buffers, coloring, flavoring and/or aromatic substances and the like), which do not deleteriously react with the active compounds or interfere with their activity. In certain embodiments, a water-soluble carrier suitable for intravenous administration is used. In some embodiments, a pharmaceutical composition can be sterile.

A suitable pharmaceutical composition, if desired, can also contain minor amounts of wetting or emulsifying agents, or pH buffering agents. A pharmaceutical composition can be a liquid solution, suspension, or emulsion.

A pharmaceutical composition can be formulated in accordance with the routine procedures as a pharmaceutical composition adapted for administration to human beings. The formulation of a pharmaceutical composition should suit the mode of administration. For example, in some embodiments, a composition for intravenous administration is typically a solution in sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachet indicating the quantity of active agent. Where a pharmaceutical composition is to be administered by infusion, it can be dispensed with an infusion bottle containing sterile pharmaceutical grade water, saline or dextrose/water. Where a pharmaceutical composition is administered by injection, an ampule of sterile water for injection or saline can be provided so that the ingredients may be mixed prior to administration.

Although the descriptions of pharmaceutical compositions provided herein are principally directed to pharmaceutical compositions that are suitable for ethical administration to humans, it will be understood by the skilled artisan that such compositions are generally suitable for administration to animals of all sorts or cells in vitro or ex vivo. Modification of pharmaceutical compositions suitable for administration to humans in order to render the compositions suitable for administration to various animals or cells in vitro or ex vivo is well understood, and the ordinarily skilled practitioner, e.g., a veterinary pharmacologist, can design and/or perform such modification with merely ordinary, if any, experimentation.

Formulations of the pharmaceutical compositions described herein may be prepared by any method known or hereafter developed in the art of pharmacology. In general, such preparatory methods include the step of bringing the active ingredient into association with a diluent or another excipient and/or one or more other accessory ingredients, and then, if necessary and/or desirable, shaping and/or packaging the product into a desired single- or multi-dose unit.

A pharmaceutical composition in accordance with the present disclosure may be prepared, packaged, and/or sold in bulk, as a single unit dose, and/or as a plurality of single unit doses. As used herein, a "unit dose" is discrete amount of a pharmaceutical composition described herein.

Exemplary Methods of Delivery

The present disclosure provides a method comprising contacting one or more host cells (e.g., mammalian cells) with a composition comprising an RNA product as described herein. In some embodiments, an RNA product is produced by a method as described herein.

In some embodiments, an RNA product in the composition is less immunostimulatory than an RNA product produced in the absence of an osmolyte, e.g., an RNA product produced in the absence of an osmolyte and at an incubation temperature of about 37° C.

In some embodiments, one or more host cells (e.g., mammalian cells) are present in a cell culture. In some embodiments, a cell culture is an in vitro cell culture. In some embodiments, a cell culture is an ex vivo cell culture.

In some embodiments, one or more host cells (e.g., mammalian cells) are present in a subject. In some embodiments, a contacting step comprises administering to the subject the composition.

In some embodiments, composition is a pharmaceutical composition as described herein. In some embodiments, a pharmaceutical composition further comprises a pharmaceutically acceptable excipient.

In some embodiments, a method as described herein increases a level of expression from the single-stranded RNA molecule(s), as compared to a level of expression from single-stranded RNA molecule(s) in an RNA product produced in the absence of the osmolyte, e.g., an RNA product produced in the absence of the osmolyte and at an incubation temperature of about 37° C.

In some embodiments, a method as described herein increases the viability of the one or more host cells (e.g., mammalian cells) following contact with the RNA product, as compared to the viability of one or more host cells (e.g., mammalian cells) contacted with an RNA product produced in the absence of the osmolyte, e.g., an RNA product produced in the absence of the osmolyte and at an incubation temperature of about 37° C.

Kits

Another aspect of the present disclosure further provides a pharmaceutical pack or kit comprising components for an in vitro transcription mixture. In some embodiments, an in vitro transcription mixture component is or comprises a wild-type bacteriophage RNA polymerase that recognizes an RNA polymerase promoter sequence. In some embodiments, an in vitro transcription mixture component is or comprises a plurality of ribonucleotides comprising at least two different types of ribonucleotides, each type comprising a different nucleoside. In some embodiments, an in vitro transcription mixture component is or comprises a transcription buffer comprising an osmolyte. In some embodiments, an osmolyte comprises an amino acid-based osmolyte, a methylamine osmolyte, a carbohydrate osmolyte, or a combination thereof.

In some embodiments, a methylamine osmolyte is or comprises glycerophosphorylcholine, trimethylamine N-oxide, or a combination thereof. In some embodiments, a carbohydrate osmolyte is or comprises sorbitol, glycerol, myonisitol, diglycerol phosphate, or a combination thereof. In some embodiments, an amino acid-based osmolyte is or comprises a proline-based osmolyte, a glycine-based osmolyte, an ectoine-based osmolyte, an alanine-based osmolyte, or a combination thereof. In some embodiments, an alanine-based osmolyte is or comprises beta-alanine. In some embodiments, an amino acid-based osmolyte is or comprises a glycine-based osmolyte. In some embodiments, a glycine-based osmolyte is or comprises betaine.

In some embodiments, a wild-type bacteriophage RNA polymerase is or comprises a wild-type T7 RNA polymerase.

Kits may be used in any applicable method, e.g., methods as described herein.

EXAMPLES

Example 1: Side-by-Side of 37° C. IVT and High Temperature IVT Using Wild-Type T7 RNA Polymerase HiScribe Polymerase Mix with or without Betaine This Example describes synthesis of RNA using exemplary methods as described herein. In particular, this Example provides that the amount of dsRNA was reduced in synthesis reactions using wild-type T7 RNA polymerase in presence of betaine.

In order to test proof of concept and/or control for any effects nucleic acid secondary structure may have on assaying dsRNA generation, high temperature IVT studies were performed using dsDNA sequence 512B, which was deemed to be unstructured (Mu, et. al, NAR 2018, which is incorporated herein by reference in its entirety).

The sequence of 512B (from 5' to 3') was as follows:

(SEQ ID NO: 1)
TAATACGACT CACTATAGGG AGAAGCTCTC TTACACCTGA

TTCATTTCCA TTGTTTTCTG CAGCAGCAAT CCGGTTTCTG

TCTTCAATTG TCAACAGTTC CTCCTCCATG CACTTATCCA

AGACGTCTCT AACTAGAAGC TTGTCCACCA GAGTGGGCTG

AAGGAGGTTC AGCAGTTGGA GATATTCATC ATGAGCGTTC

TCAAACGATG GAGAGGGCAA GTCCGTGAGC TCAGGGTTCA

TGTAGCGGGC GGCCAGAGGG CTGCCGGTTC TCCGGAGGGC

CTCCACGAAT TCCCGAGTCC AACCAAGGTG CCAGACTCCC

TTCTCCAAGG TGCTCAGCAG CAGTTCAACT GCCTGCATGT

TCCCGGAGGT GGCGACTGTC CTCTGAATCT GCTCCTTCAC

CTCTGCAGGC AGAAAGGTCA GGTAGTCCAG CACAGGCTCC

ACCTGGATGT ACATTTTCAC CCTGGCCCTG AAGCACGAGA

TGAGATAGCG GAAATTCTCG TCTGTGGAAT ACCCATTCGA

CATTCTCCC dsDNA 512B IVT template was generated by PCR amplification of an IDT plasmid intermediate from which 512B ssDNA was produced. Amplification was carried out in a 20 µL reaction consisting of 0.25 µM each primer 512B T7 fwd and 512B rev, 1× Herculase II buffer, 250 uM each dNTP, 10 ng 512B plasmid (Integrated DNA Technologies), and 0.4 µL Herculase II enzyme. PCR product was purified with QiaQuick PCR Clean Up Kit (Qiagen) and eluted into 30 µL 10 mM Tris-Cl pH 8.5. The entirety of the eluted product was subjected to treatment with 125 U of Dpn1 enzyme (New England Biolabs) in a 50 µL reaction to digest template plasmid. The digested product was purified with a Clean and Concentrator-5 (Zymo Research) and eluted into 10 µL 10 mM Tris-HCl pH 8.5.

A 10 µL control reaction, representative of commercially available high yield IVT conditions, consisted of 100 ng Luc2 T7 template, 5 mM each NTP, 1× HiScribe Transcription Buffer, and 1 µL HiScribe polymerase mix (NEB) and was incubated at 37 C for 2 hours. High temperature IVT was tested at both 45° C. and 50° C. with or without 2M Betaine supplementation. These reactions consisted of the same reaction set up as the 37° C. control reaction with or without the addition of 2M Betaine. Reactions were subsequently incubated at respective temperatures for 2 hrs.

RNA concentration was determined using the RNA application on a NanoDrop OneC instrument (Thermo Scientific).

TABLE 1

| IVT Synthesis Condition | RNA concentration (ng/µL) |
| --- | --- |
| 37° C. Control | 2301.1 |
| 45° C., 0M betaine | 125.3 |
| 45° C., 2M betaine | 2343.6 |
| 50° C., 0M betaine | 17.8 |
| 50° C., 2M betaine | 2104.3 |

To assay the relative concentrations of dsRNA contaminants in each IVT preparation, an adapted protocol of the Viral dsRNA Detection kit (CisBio) was followed. The dsRNA detection kit used was commercially available from CisBio as an assay for detecting viral genome replication in cell lysates. The kit used a sandwich assay of two dsRNA detecting antibodies. The first was labelled with Europium Cryptate donor and the second with d2 acceptor. 10 µL of a 1:50 dilution mix of each antibody was added to a solution of 10 µL total RNA and incubated overnight at 4° C. Binding of dsRNA by both antibodies in close proximity, and excitation of the donor with 330 nm wavelength light, triggers Fluorescence Resonance Energy Transfer (FRET) toward the acceptor which fluoresces at an emission wavelength of 665 nm. Calculating the ratio of acceptor emission signal at 665 nm to donor emission signal at 620 nm provided a raw signal intensity value that is proportional to dsRNA concentration. All ratios were multiplied by a factor of 104 to obtain a processed signal intensity value that can be used for data analysis. (Viral Double-stranded RNA Detection Kit, CisBio, 64RNAPEG.)

All RNA samples were diluted to a working concentration of 100 ng/uL total RNA in 40 µL 1× Lysis Buffer (Cisbio). 1:4 series dilutions in 1× lysis buffer were carried out for each sample to a minimum concentration of 0.391 ng/μL. Antibody solution was made by mixing 400 uL of a 1:50 dilution of each antibody in Detection Buffer (Cisbio). 10 μL antibody solution was added to 10 μL of each RNA dilution series in duplicate and incubated at 4° C. overnight in a low volume 96 well assay plate (Cisbio). Total dsRNA in each reaction was assayed by calculating the ratio of signal at 665 nm (acceptor emission) to signal at 620 nm (donor emission) and multiplied by a factor of 104 as described in the Viral dsRNA Detection kit. Processed signal ratios at each total RNA concentration were plotted on a scatter plot. One possible limitation of the assay was that high concentrations of dsRNA may result in false negatives from lower signal ratios since saturation with dsRNA results in binding of antibodies at too far of a distance from each other to trigger FRET. However, the assay was useful for assessing the relative difference in dsRNA amount between samples. As shown in FIG. 1, the presence of Betaine in the samples correlated with a reduction in the amount of dsRNA.

Example 2: Comparison of RNA Products Produced According to Exemplary Method Described Herein to Commercially Available High Temperature Transcription Reaction This Example describes a comparison of an exemplary RNA synthesis method as described herein with a comparable method using commercially available high temperature transcription reaction components. This Example demonstrates that exemplary RNA synthesis compositions and methods as described herein performed as well as, if not slightly better than, a commercially available reaction kit and method.

The luc2 gene encoding an optimized version of firefly luciferase was amplified from pGL4.10[luc2] (Promega). Amplification was carried out at an annealing temperature of 70° C. in a 20 μL reaction consisting of 0.25 μM each primer Luc2_fwd and Luc2_rev, 1× Herculase II buffer, 25 mM each dNTP, 30 ng pGL4.10[luc2] plasmid (Promega), 0.25M Betaine and 0.4 μL Herculase II enzyme. PCR product was purified with QiaQuick PCR Clean Up Kit (Qiagen) and eluted into 30 μL 10 mM Tris-HCl pH 8.5. The entirety of the eluted product was subjected to treatment with 125 U of Dpn1 enzyme (New England Biolabs) in a 50 L reaction to digest template plasmid. The digested product was purified with a QiaQuick PCR Clean Up Kit (Qiagen) and eluted into 50 μL 10 mM Tris-HCl pH 8.5. This digested, primary PCR product was then amplified at 50 C in a 20 μL reaction consisting of 0.25 μM each primer T7-GGG_fwd and 120 pA_rev, 1× Herculase II buffer, 25 mM each dNTP, 10 ng Luc2 primary amplification product, and 0.4 μL Herculase II enzyme. This secondary PCR product was cleaned up using QiaQuick PCR Clean Up Kit (Qiagen) and eluted into 30 uL 10 mM Tris-HCl pH 8.5. Eluted PCR product was then run at a concentration of 50 ng/μL in 20 uL of water across 10 lanes of a 1% EX gel (Thermo Scientific) for 10 minutes. The main band was excised and processed using a QiaQuick Gel Isolation Kit. Gel isolated product was eluted into 50 μL 10 mM Tris HCl pH 8.5. To further concentrate the template, eluted product was cleaned up again with DNA Clean & Concentrator-5 (Zymo Research) into 10 μL of 10 mM Tris-HCl pH 8.5.

The sequences of primers used were as follows:

```
Luc2_fwd
                                        (SEQ ID NO: 2)
CTTGTTCTTT TTGCAGAAGC TCAGAATAAA CGCTCAACTT TGGCCACCat ggaagatgcc aaaaacatta agaagggc Luc2_rev
                                        (SEQ ID NO: 3)
AGAATGTGAA GAAACTTTCT TTTTATTAGG AGCAGATACG

AATGGCTACA TTTTGGGGGA CAACATTTTG TAAAGTGTAA

GTTGGTATTA TGTAGCTTAG AGACTCCATT CGGGTGTTCT

TGAGGCTGGT CTATCATTAc acggcgatct tgccgcc

T7-GGG_fwd
                                        (SEQ ID NO: 4)
gaattTAATA CGACTCACTA TAGGGcttgt tcttttgca gaagc 120pA_rev
                                        (SEQ ID NO: 5)
TTTTTTTTTT TTTTTTTTTT TTTTTTTTTT TTTTTTTTTT

TTTTTTTTTT TTTTTTTTTT TTTTTTTTTT TTTTTTTTTT

TTTTTTTTTT TTTTTTTTTT TTTTTTTTTT TTTTTTTTTT agaatgtgaa gaaactttct ttttattag
```

A 20 μL control reaction, representative of commercially available high yield IVT conditions, consisted of 150 ng luc2 T7 template, 7.5 mM each NTP, 1× HiScribe Transcription Buffer, and 2 uL HiScribe polymerase mix (NEB) and incubated at 37° C. for 2 hours. The 50° C. HiScribe reaction with 2M betaine supplementation consisted of the same reagents as the 37 C IVT control reaction except for the addition of 2M betaine. This was subsequently incubated at 50° C. for 2 hrs.

To compare the product of our high temperature manufacturing method to that of commercially available high temperature transcription reagents, IVT RNA produced from a custom-made proprietary high yield formulation of a Hi-T7 polymerase mix (NEB) was compared to that produced using the commercial reagents. Previous studies (unpublished) found better transcription quality from such a polymerase mix in an in-house T7 buffer formulation compared to the proprietary buffer formulation obtained from NEB. A 20 μL transcription reaction using NEB's proprietary High Yield Hi-T7 polymerase mix included 150 ng Luc2 T7 template, 7.5 mM each NTP, 1× in-house T7 transcription buffer, and 2 μL proprietary high yield formulation of Hi-T7 polymerase mix (NEB). The reaction was incubated at 50 C for 2 hours.

All IVT products were cleaned up using Monarch 50 μg RNA Clean Up kit (NEB) and eluted into 40 μL nuclease-free water. Eluted products were then digested in 50 μL reactions consisting of 1× DNase I buffer and 5 U of DNase I (RNase-free) (New England Biolabs) at 37° C. for 15 minutes to degrade DNA template. DNase I treated samples were cleaned up using Monarch 50 ug RNA Clean Up kit (New England Biolabs) and eluted into 40 L nuclease-free water.

The DNAse I treated products were enzymatically capped using Vaccinia Capping Enzyme kits with 2'-O-methyltransferase (NEB) to produce mRNAs with a naturally occurring 2'-O-methlyated 5' m7G cap for optimal expression in A549 cell culture experiments. Prior to capping, each IVT RNA was denatured at 65 C for 5 minutes and immediately place on ice for 2 minutes in order to denature any 5' secondary structure that could inhibit capping. Each 20 uL capping reaction consisted of 6 ug IVT RNA, 1× capping buffer, 0.5 mM GTP, 0.2 mM SAM, 10 U Vaccinia Capping Enzyme, and 50 U mRNA Cap 2'-O-methyltransferase (NEB). Capping reactions were incubated at 37 C for 1 hour.

All capped mRNAs were cleaned up using Monarch 10 ug RNA Clean Up kit (NEB) and eluted into 10 uL nuclease-free water. Concentrations are listed in Table 2.

TABLE 2

| IVT Synthesis Method | RNA concentration (ng/uL) |
| --- | --- |
| HiScribe at 37° C.: | 547.8 ng |
| HiScribe + 2M betaine at 50° C. | 575.3 |
| NEB Hi-T7 Polymerase at 50° C. | 520.9 |

Example 3: In Vitro Transcription at 50° C. with Betaine Concentration Gradient

This Example describes exemplary RNA synthesis compositions and methods as described herein using different betaine concentrations. This Example demonstrates that increasing betaine concentrations in transcription reactions performed at 50° C. resulted in increasing amounts of RNA product.

20 μL in vitro Transcription reactions containing 200 ng T7 template, 5 mM each NTP, 1× HiScribe Transcription Buffer, and 2 uL HiScribe polymerase mix (NEB) were supplemented with 0M, 0.5M, 1M, or 2M betaine and incubated at 50° C. for 1 hour.

All IVT products were cleaned up using Monarch 500 μg RNA Clean Up kit (NEB) and eluted into 40 μL nuclease-free water. Eluted products were then digested in 50 μL reactions consisting of 1× DNase I buffer and 5 U of DNase I (RNase-free) (New England Biolabs) at 37° C. for 15 minutes to degrade DNA template. DNase I treated samples were cleaned up using Monarch 500 ug RNA Clean Up kit (New England Biolabs) and eluted into 50 L nuclease-free water. Concentrations of the products of each reaction containing either 0M, 0.5M, 1M, or 2M betaine are presented in Table 3.

RNA concentration was determined using the RNA application on a NanoDrop OneC instrument (Thermo Scientific).

TABLE 3

| Betaine Concentration | RNA concentration (ng/uL) |
| --- | --- |
| 0M | 61.4 |
| 0.5M | 190.5 |
| 1M | 1396.4 |
| 2M | 1853.2 |

Example 4: A549 Cell Culture Methods

Figure 2:
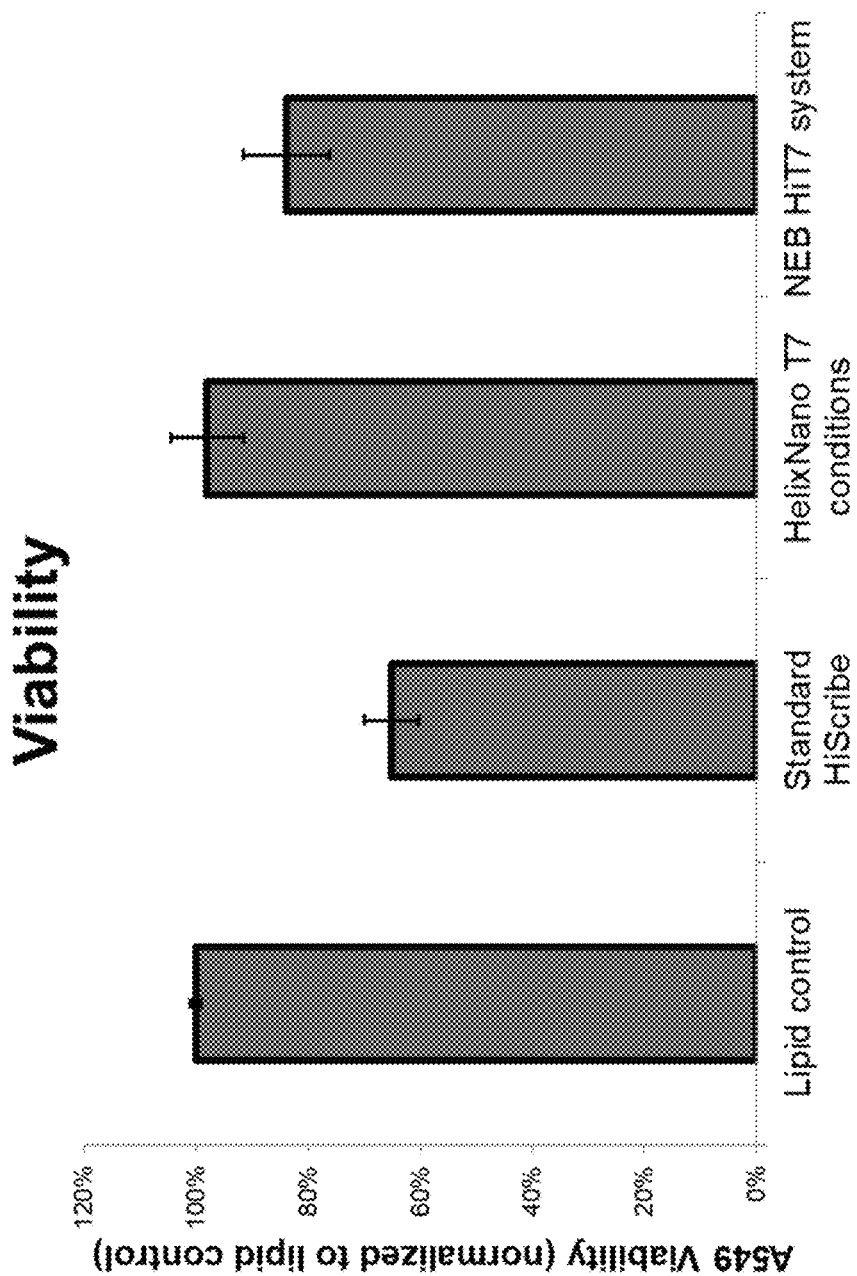
FIG. 2 includes a bar graph showing viability of A549 cells following transfection with RNA molecules synthesized using different transcription methods, including an exemplary method as described herein.
Figure 3:
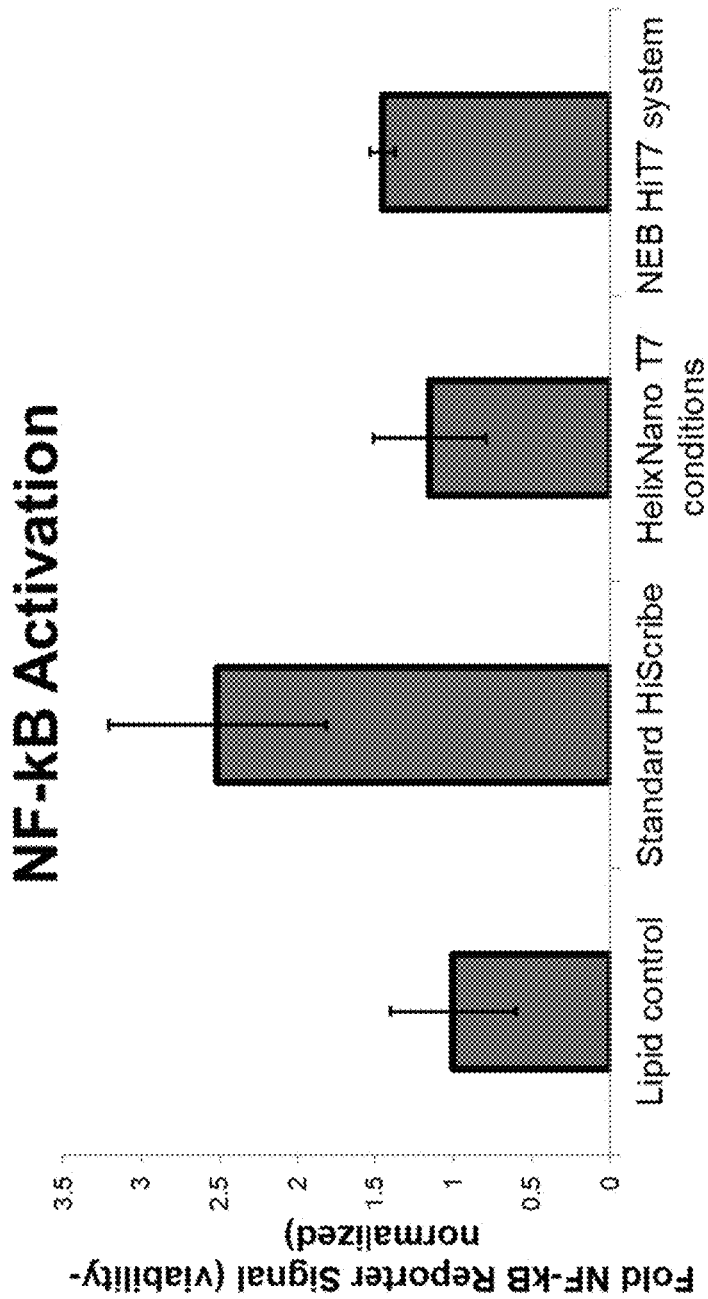
FIG. 3 includes a bar graph showing NF-kB reporter activation by RNA molecules synthesized using different transcription methods, including an exemplary method as described herein.
Figure 4:
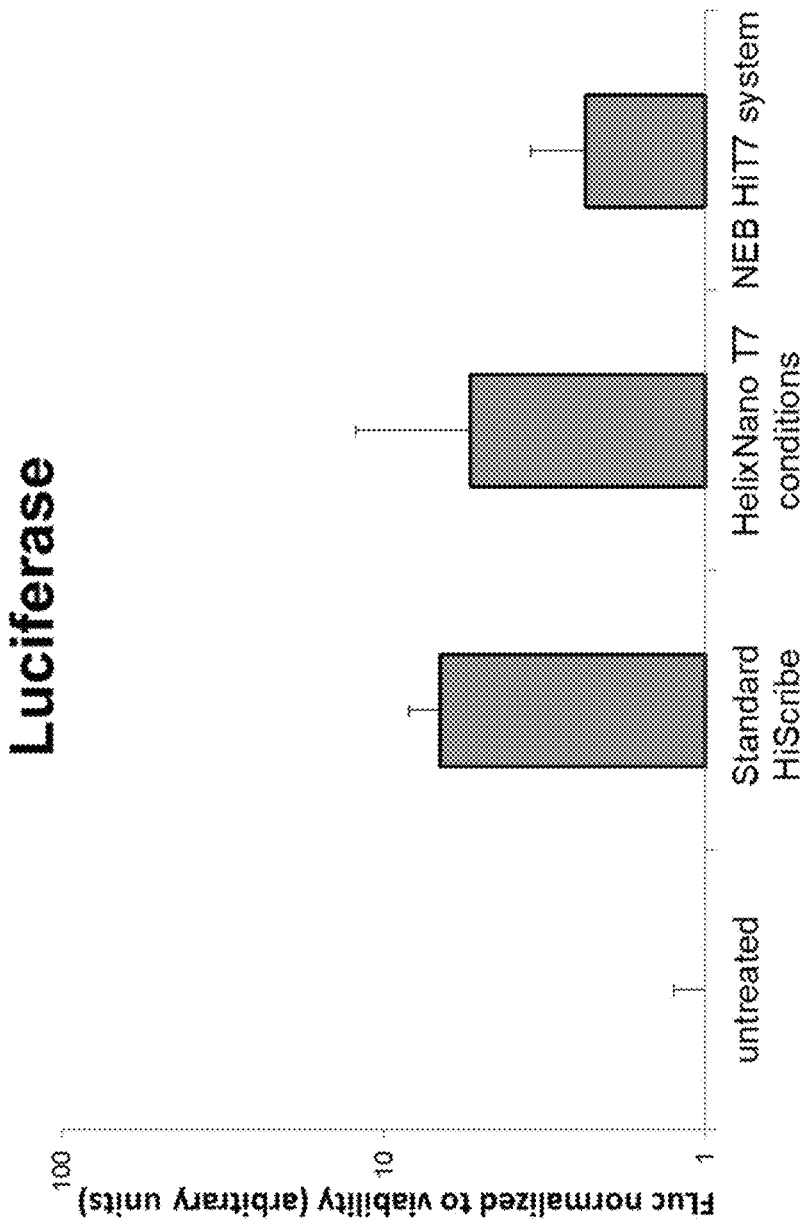
FIG. 4 includes a bar graph showing luciferase signal in A549 cells transfected with FLuc mRNA synthesized using different transcription methods, including an exemplary method as described herein.

This Example describes the effects observed in cells (e.g., A549 cells) when transfected with RNA products synthesized using exemplary RNA synthesis compositions and methods as described herein. A549-Dual were cultured in high glucose GlutaMAX Dulbecco's Modified Eagle Medium supplemented with 10% heat-inactivated fetal bovine serum, 100 units/mL penicillin, 100 μg/mL streptomycin, 10 μg/mL blasticidin, and 100 μg/mL zeocin and maintained at 37° C. and 5% C02. Cells were plated to a 96-well at 6,000 cells/well 1 d prior to transfection. 100 ng of each mRNA were transfected using TransIT-mRNA Transfection Kit (MirusBio) using 2 μL mRNA Boost Reagent: 1 μg mRNA and 2 μL TransIT-mRNA Reagent: 1 μg mRNA. Transfections were performed in duplicate. Results obtained are shown in FIGS. 2, 3, and 4. Viability and luciferase expression were determined using the ONE-Glo+Tox Luciferase Reporter and Cell Viability Assay (Promega). NF-κB activation was measured via the SEAP reporter gene using the QUANTI-Blue detection reagent (InvivoGen) as described by the manufacturer.

Example 5: Discussion of Results Obtained

Table 1 above shows that RNA yield was significantly decreased when in vitro transcription was performed at a temperature of higher than 37° C. in the absence of any osmolyte (e.g., betaine), while osmolyte (e.g., betaine) supplementation significantly improved RNA yield at such a high temperature. Table 3 further shows the relationship between osmolyte concentration (e.g., betaine concentration) and IVT yield at 50° C. For example, Table 3 shows that in some embodiments, 0.5M osmolyte (e.g., betaine) supplementation provides an improvement in RNA yield compared to no supplementation. In some embodiments, osmolyte(s) may be present in an in vitro transcription buffer mixture at a concentration of at least 0.1M or higher, including, e.g., at least 0.2M, at least 0.3M, at least 0.4M, at least 0.5M, at least 0.6M, at least 0.7M, at least 0.8M, at least 0.9M, at least 1M, at least 1.5M, at least 2M, at least 2.5M, at least 3M, at least 3.5M, at least 4M, at least 4.5M, at least 5M, at least 5.5M, at least 6M, at least 6.5M, at least 7, at least 7.5M, at least 8M, at least 8.5M, at least 9M, at least 9.5M, at least 10M, or higher.

FIG. 1 shows the reduction in dsRNA that results from in vitro transcription at an elevated temperature (e.g., a temperature of higher than 37° C. or higher). The data shown reflects the amount of dsRNA at different dilution factors of sample obtained from each indicated synthesis method. One possible limitation of the assay was that high concentrations of dsRNA can result in false negatives from lower signal ratios since saturation with dsRNA results in binding of antibodies at too far of a distance from each other to trigger FRET. However, the difference in dsRNA amount is evident in the lower range of total RNA for each sample. It appears that transcription at 45° C. by itself reduces dsRNA amount, but without wishing to be bound by a particular theory, in some embodiments, the transcription yield at 45° C. may be low for large scale synthesis. In some embodiments, in vitro transcription with osmolyte (e.g., betaine) supplementation at a temperature of 50° C. allows for both high yield synthesis and low dsRNA amounts as compared to that of 45° C. IVT synthesis without osmolyte (e.g., betaine).

The effects of this reduction in dsRNA, compared to the high amounts from 37° C. in vitro transcription, are evident from the data presented in FIGS. 2, 3, and 4. Improved viability is showed in FIG. 2 whereas reduced immunogenicity is exhibited in FIG. 3. Comparable luciferase expression is observed from all synthesis methods in FIG. 4. The addition of osmolytes, such as betaine, to high temperature in vitro transcription reactions that use, for example, wild-type bacteriophage RNA polymerase, is useful for producing high yields of RNA with reduced immunogenicity and/or toxicity.

EQUIVALENTS

In general, terms used herein are in accordance with their understood meaning in the art, unless clearly indicated otherwise. It is to be appreciated by those skilled in the art that various alterations, modifications, and improvements to the present disclosure will readily occur to those skilled in the art. Such alterations, modifications, and improvements are intended to be part of the present disclosure, and are intended to be within the spirit and scope of the invention. Accordingly, the foregoing description and drawing are by way of example only and any invention described in the present disclosure if further described in detail by the claims that follow.

Those skilled in the art will appreciate typical standards of deviation or error attributable to values obtained in assays or other processes as described herein. The publications, websites and other reference materials referenced herein to describe the background of the invention and to provide additional detail regarding its practice are hereby incorporated by reference in their entireties.

It is to be understood that while embodiments of the invention have been described in conjunction with the detailed description thereof, the foregoing description is intended to illustrate and not limit the scope of the invention, which is defined by the scope of the appended claims. The scope of the present invention is defined by the claims appended hereto and is not limited by certain embodiments described herein. Other aspects, advantages, and modifications are within the scope of the following claims.

What is claimed is:

1. A method of producing an RNA product comprising a step of:
   incubating an in vitro transcription mixture, thereby producing an RNA product that comprises a plurality of single-stranded RNA molecules,
   wherein the in vitro transcription mixture comprises:
   (i) a DNA template comprising an RNA polymerase promoter sequence operatively linked to a target sequence;
   (ii) at least one RNA polymerase that recognizes the RNA polymerase promoter sequence, wherein the at least one RNA polymerase is or comprises a wild-type bacteriophage RNA polymerase;
   (iii) a plurality of ribonucleotides comprising at least two different types of ribonucleotides, each type comprising a different nucleoside; and
   (iv) a transcription buffer comprising an osmolyte; and
   wherein the incubating step occurs at a temperature of about 45° C. or higher.

2. The method of claim 1, wherein the osmolyte is or comprises an amino acid-based osmolyte, a methylamine osmolyte, a carbohydrate osmolyte, or a combination thereof.

3. The method of claim 2, wherein the methylamine osmolyte is or comprises glycerophosphorylcholine, trimethylamine N-oxide, or a combination thereof.

4. The method of claim 2, wherein the carbohydrate osmolyte is or comprises sorbitol, glycerol, myonisitol, diglycerol phosphate, or a combination thereof.

5. The method of claim 2, wherein the amino acid-based osmolyte is or comprises a proline-based osmolyte, a glycine-based osmolyte, an ectoine-based osmolyte, an alanine-based osmolyte, or a combination thereof.

6. The method of claim 5, wherein the alanine-based osmolyte is or comprises beta-alanine.

7. The method of claim 2, wherein the amino acid-based osmolyte is or comprises a glycine-based osmolyte.

8. The method of claim 7, wherein the glycine-based osmolyte is or comprises betaine.

9. The method of claim 8, wherein betaine is present in the in vitro transcription mixture at a concentration of about 0.5M to about 10M, or about 2M to about 5M.

10. The method of claim 1, wherein the bacteriophage RNA polymerase is a T7 RNA polymerase, a T3 RNA polymerase, a SP6 RNA polymerase, a N4 virion RNA polymerase, or a variant thereof.

11. The method of claim 1, wherein the bacteriophage RNA polymerase is or comprises a T7 RNA polymerase.

12. The method of claim 1, wherein the incubating step occurs at a temperature of about 46° C., about 47° C., about 48° C., about 49° C., about 50° C., about 51° C., about 52° C., about 53° C., about 54° C., about 55° C., or higher.

13. The method of claim 1, wherein the plurality of single-stranded RNA molecules are or comprise:
   (a) guide RNA, short hairpin RNA, siRNA, microRNA, long non-coding RNA, or messenger RNA (mRNA);
   (b) mRNA molecules encoding one or more target polypeptides;
   (c) one or more ribonucleotides that each include a modified nucleoside; or
   (d) any combination thereof.

14. The method of claim 1, wherein the RNA product:
   (a) is less immunostimulatory than an RNA product produced in the absence of the osmolyte at an incubation temperature of about 37° C.;
   (b) has a lower level of double-stranded RNA than that in an RNA product produced in the absence of the osmolyte at an incubation temperature of about 37° C.;
   (c) has a higher amount of the single-stranded RNA molecules than that in an RNA product produced in the absence of the osmolyte at an incubation temperature of about 37° C.; or
   (d) any combination thereof.

15. The method of claim 14, wherein the method of (b) does not comprise a step of removing any double-stranded RNA from the RNA product.

16. The method of claim 1, wherein the DNA template is immobilized on a solid substrate.

17. The method of claim 1, wherein the plurality of single-stranded RNA molecules each have a length of:
(a) at least 100 nucleotides or longer;
(b) no more than 200,000 nucleotides; or
(c) both (a) and (b).

18. The method of claim 1, wherein the incubating step is performed for a time sufficient for a target sequence to be transcribed to a single-stranded RNA molecule.

19. The method of claim 18, wherein the incubating step is performed for at least 1 hour.

* * * * *

SEQUENCE LISTING

```
<160> NUMBER OF SEQ ID NOS: 5

<210> SEQ ID NO 1
<211> LENGTH: 529
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
taatacgact cactataggg agaagctctc ttacacctga ttcatttcca ttgttttctg    60
cagcagcaat ccggtttctg tcttcaattg tcaacagttc ctcctccatg cacttatcca   120
agacgtctct aactagaagc ttgtccacca gagtgggctg aaggaggttc agcagttgga   180
gatattcatc atgagcgttc tcaaacgatg gagagggcaa gtccgtgagc tcagggttca   240
tgtagcgggc ggccagaggg ctgccggttc tccggagggc ctccacgaat tcccgagtcc   300
aaccaaggtg ccagactccc ttctccaagg tgctcagcag cagttcaact gcctgcatgt   360
tcccggaggt ggcgactgtc ctctgaatct gctccttcac ctctgcaggc agaaaggtca   420
ggtagtccag cacaggctcc acctggatgt acattttcac cctggccctg aagcacgaga   480
tgagatagcg gaaattctcg tctgtggaat acccattcga cattctccc                529

<210> SEQ ID NO 2
<211> LENGTH: 78
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cttgttcttt ttgcagaagc tcagaataaa cgctcaactt tggccaccat ggaagatgcc    60
aaaaacatta agaagggc                                                   78

<210> SEQ ID NO 3
<211> LENGTH: 157
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
agaatgtgaa gaactttct ttttattagg agcagatacg aatggctaca ttttggggga    60
caacattttg taaagtgtaa gttggtatta tgtagcttag agactccatt cggtgttct   120 tgaggctggt ctatcattac acggcgatct tgccgcc                            157
```

-continued

```
<210> SEQ ID NO 4
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gaatttaata cgactcacta tagggcttgt tcttttttgca gaagc              45

<210> SEQ ID NO 5
<211> LENGTH: 149
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tttttttttt tttttttttt tttttttttt tttttttttt tttttttttt tttttttttt    60
tttttttttt tttttttttt tttttttttt tttttttttt tttttttttt tttttttttt   120
agaatgtgaa gaaactttct ttttattag                                     149
```